United States Patent [19]
Griffith

[11] Patent Number: 5,000,178
[45] Date of Patent: Mar. 19, 1991

[54] SHIELDED ELECTROMAGNETIC TRANSDUCER

[75] Inventor: Neil J. Griffith, San Diego, Calif.

[73] Assignee: LTI Biomedical, Inc., San Diego, Calif.

[21] Appl. No.: 170,361

[22] Filed: Mar. 18, 1988

Related U.S. Application Data

[63] Continuation-in-part of Ser. No. 866,877, May 23, 1986, abandoned.

[51] Int. Cl.⁵ .............................................. A61N 1/00
[52] U.S. Cl. .............................. 128/419 F; 128/82.1; 600/13
[58] Field of Search .............. 128/419 F, 82.1, 419 R; 600/9, 10, 11, 13, 14, 15

[56] References Cited

U.S. PATENT DOCUMENTS

| | | | |
|---|---|---|---|
| 3,890,953 | 6/1975 | Kraus et al. | 128/1.5 |
| 3,893,462 | 7/1975 | Manning | 128/421 |
| 3,952,751 | 4/1976 | Yarger | 128/422 |
| 4,066,065 | 1/1978 | Kraus | 128/1.5 |
| 4,266,532 | 5/1981 | Ryaby et al. | 128/1.5 |
| 4,266,533 | 5/1981 | Ryaby et al. | 128/1.5 |
| 4,432,361 | 2/1984 | Christensen et al. | 128/419 F |
| 4,467,808 | 8/1984 | Brighton et al. | 128/419 R |
| 4,467,809 | 8/1984 | Brighton | 128/419 F |
| 4,501,265 | 2/1985 | Pescatore | 128/419 F |
| 4,509,520 | 4/1985 | Dugot | 128/419 F |
| 4,535,775 | 8/1985 | Brighton et al. | 128/419 F |
| 4,548,208 | 10/1985 | Neimi | 128/419 F |
| 4,574,809 | 3/1986 | Talish et al. | 128/419 F |
| 4,587,957 | 5/1986 | Castel | 128/1.3 |
| 4,619,264 | 10/1986 | Singh | 128/419 F |
| 4,620,543 | 11/1986 | Heppenstall et al. | 128/419 F |
| 4,641,633 | 2/1987 | Delgado | 128/1.3 |
| 4,654,574 | 3/1987 | Thaler | 128/419 F |
| 4,674,482 | 6/1987 | Waltonen et al. | 128/1.5 |

FOREIGN PATENT DOCUMENTS 935110  6/1982  U.S.S.R. .......................... 128/419 F

OTHER PUBLICATIONS

Fish, "Healing with Electronics," *Radio-Electronics*, 57, 4, 78 et seq. (Apr. 1986).
Brighton et al. (III), "Fracture Helaing in the Rabbit Fibula when Subjected to Various Capacitively Coupled Electrical Fields," *J. Orthopaedic Res*, 3, 3, 331–340 (1985).
Ohashi et al., "The Electric Current Ration of the Bone in the Rabbit Thigh for Capactively Coupled Electric Field," *Brags*, (Boston, Mass.: Oct. 13–17, (1985).
(List continued on next page.)

*Primary Examiner*—Francis Jaworski
*Assistant Examiner*—George Manuel
*Attorney, Agent, or Firm*—Brown, Martin, Haller & McClain

[57] ABSTRACT

An electrical to electromagnetic transducer for applying electromagnetic energy to damaged potions of the living body, which provides high efficiency generation of electromagnetic fields for electromagnetic therapy by directing electromagnetic radiation to the damaged body part. Electromagnetic radiation is initially generated by a dipole consisting of a bar of high permeability material wrapped with an electrically conductive coil. The dipole is placed between a conductive shield and the damaged body part. An electrical signal passes through the coil which causes a magnetic field to be generated through and around the high permeability material. The field radiation pattern of the dipole is directed toward the damaged body part by a conductive shield. Magnetic fields which are generated away from the damaged body part intersect the conductive shield and establish eddy currents. These eddy currents in turn generate magnetic fields opposite and nearly equal to the magnetic fields generated by the electromagnetic source. These resultant redirected electromagnetic fields then reinforce the electromagnetic field directed towards the damaged body part and diminish the electromagnetic field directed away from the damaged body part.

51 Claims, 7 Drawing Sheets

OTHER PUBLICATIONS

Spadaro, "Bioelectrical Stimulation of Bone Formation: Methods, Models, and Mechanisms," *J. Bioelectricity*, 1, 1, 99–128 (1982).

Bassett et al., "Treatment of Osteonecrosis of the Hip with Specific, Pulsed Electromagnetic Fields (PEMFs): A Preliminary Clinical Report," Chaper 56 of *Bone Circulation* (Arlet et al., ed., 1984).

Frank et al., "A Review of Electromagnetically Enhanced Soft Tissue Healing," *IEEE Engineering in Med. and Biol. Mag.*, 2, 4, 27–32 (Dec., 1983).

Black, "Electrical Stimulation of Hard and Soft Tissues in Animal Models," Clinics in Plas. Surg., 12, 2, 243–257 (1985).

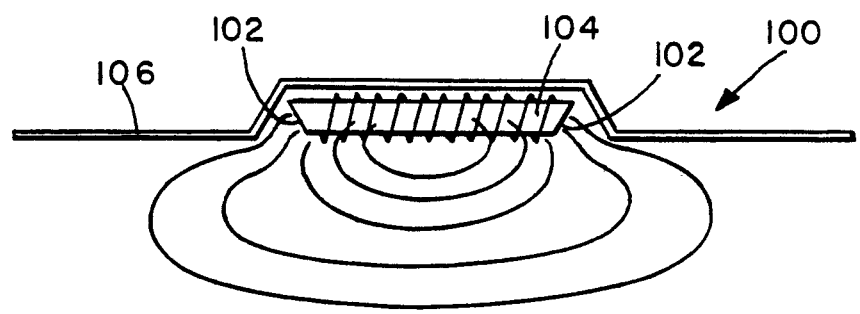
FIG. 14
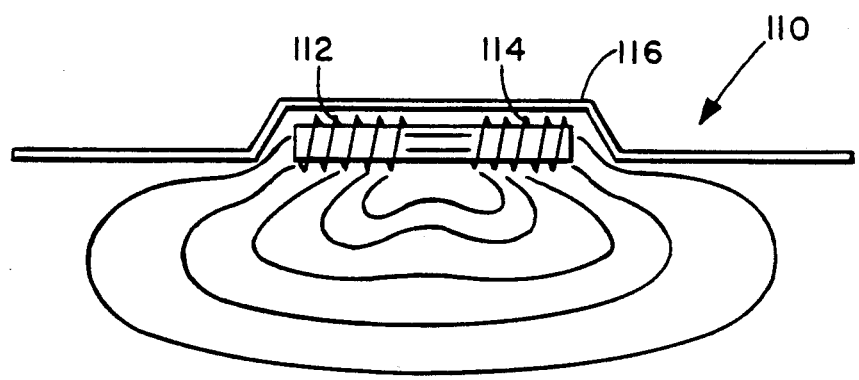
FIG. 15
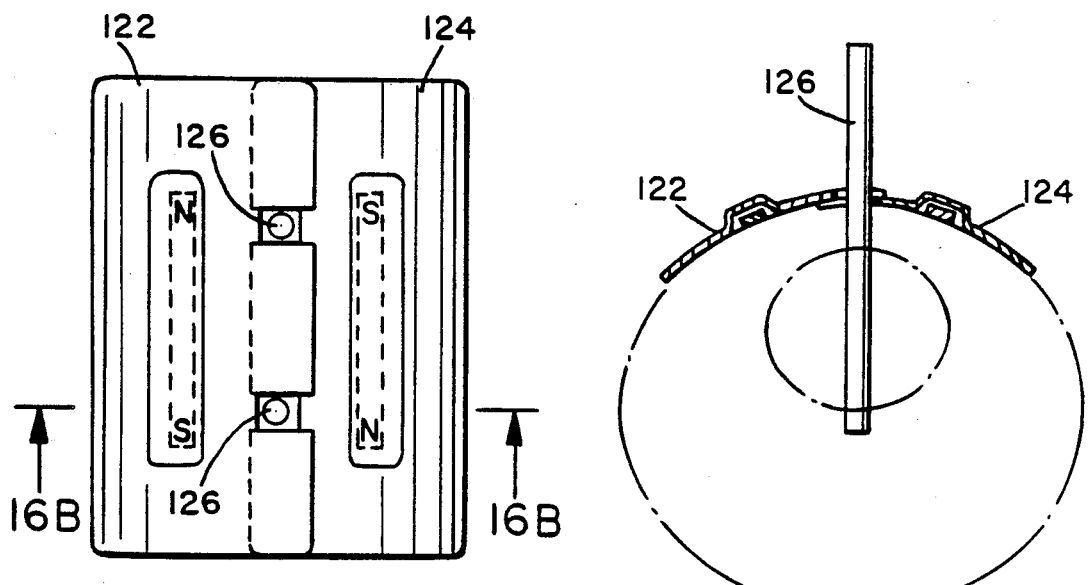
FIG. 16A
FIG. 16B

SHIELDED ELECTROMAGNETIC TRANSDUCER

RELATED APPLICATIONS

This application is a continuation-in-part of Ser. No. 866,877 filed May 23, 1986 now abandoned.

FIELD OF THE INVENTION

The present invention relates to the field of transducers for converting electrical energy into electromagnetic radiation. More specifically, the present invention relates to the use of transducers to provide electromagnetic energy to damaged body components to promote healing.

BACKGROUND OF THE INVENTION

The use of electric or electromagnetic fields to promote healing, particularly the healing of fractured bones, has been investigated since the early 19th Century. See Spadaro, "Bioelectric Stimulation of Bone Formation: Methods, Models and Mechanisms," *Journal of Bioelectricity*, 1(1), 99-128 (1982). In early research, direct current techniques were used by applying electrodes to the skin or via the use of implanted electrodes into the bone. More recently, mechanisms which encourage growth have been investigated which involve the use of electromagnetic fields to induce voltage and current effects within the tissue. These techniques have been particularly useful in non-healing or "nonunion" fractures by inducing bones to heal which will not heal naturally.

An example of a technique for the use of electromagnetic radiation to promote bone growth is Ryaby et al., U.S. Pat. No. 4,266,532, issued May 12, 1981. Ryaby et al. showed effective techniques for promoting bone growth. However, the techniques disclosed in Ryaby et al. required the use of power applied from a standard wall socket. Electromagnetic therapy is only useful so long as the patient uses it. Being tethered to the wall is a sufficient annoyance such that many patients will not follow the electrotherapy regimen prescribed by their doctors.

Recognizing this problem, a great deal of work has occurred to try to develop mechanisms whereby portable electrotherapy may be provided. Examples of such techniques are shown in Talish, et al., U.S. Pat. No. 4,574,809, issued Mar. 11, 1986; Christianson et al., U.S. Pat. No. 4,432,361, issued Feb. 21, 1984, Castel, U.S. Pat. No. 4,587,957, issued May 13, 1986; and co-pending application Ser. No. 899,674 assigned to the Assignee of the present patent application. Christianson et al. requires the use of invasive electrical probes into the bone. It is desirable to avoid invasive techniques if possible because of the possibility of infection. Talish et al., Castel and Serial No. 899,674 use magnetic transducers designed to provide a uniform electromagnetic field throughout the treatment area. Talish et al. uses a Helmholtz coil as does Ryaby et al. Ser. No. 899,674 uses a solenoid surrounding the injured limb to generate the magnetic field. Castel uses a polarized magnetic field. These types of transducers generate a great deal of electromagnetic radiation outside of the damaged body portion and waste a great deal of energy inside the damaged body portion by radiating areas where radiation is unnecessary. For example, the tibia and scaphoid bones are very close to the surface of the skin. Use of the techniques shown in the above references causes radiation to be generated throughout the entire limb even though the damaged portion is close to the surface of the skin. This problem is even more striking in the case of bones in the trunk of the body such as vertebrae and ribs. Therefore, the technique for applying electromagnetic fields in a manner which concentrates their application on the desired area while minimizing wasted electromagnetic energy is desirable.

The benefits of electromagnetic stimulation of damaged or diseased tissue are being further developed and are widely accepted by today's scientific community. Examples of studies which show the benefits of electromagnetic stimulation to soft tissue as well as bone are Black, "Electrical Stimulation of Hard and Soft Tissues in Animal Models," *Clinics in Plastic Surgery*, Vol. 12, No. 2, pages 243-257 April, 1985 and Frank et al., "A Review of Electromagnetically Enhanced Soft Tissue Healing," IEEE *Engineering in Medicine and Biology Magazine*, pages 211-32 December, 1983. In addition, diseased rather than broken bones may benefit from electromagnetic therapy. For example, see Brighton, U.S. Pat. No. 4,467,808, and Bassett et al., "Treatment of Osteonecrosis of the Hip with Specific Pulsed Electromagnetic Fields (PEMFs): A Preliminary Clinical Report," *Bone Circulation*, Chapter 56 pages 343-357, edited by Arlet, Ficat and Hungerford (1984).

SUMMARY OF THE INVENTION

The present invention provides an electrical to electromagnetic transducer for applying electromagnetic energy to damaged portions of the living body. The electromagnetic radiation stimulates healing and helps provide quicker recovery. The embodiments of the present invention provide high efficiency generation of electromagnetic waves for electromagnetic therapy by directing electromagnetic radiation to the damaged body part. In one embodiment, the electromagnetic radiation is initially generated by a dipole consisting of a bar of high permeability material wrapped with an electrically conductive coil. An electrical signal passes through the coil which causes a magnetic field to be generated through the high permeability material. The field radiation pattern of the dipole is directed towards the damaged body part by a conductive shield. The electromagnetic field generator is placed between the conductive shield and the damaged body part. Magnetic fields which are generated away from the damaged body part intersect with the conductive shield. The change in the magnetic field establishes eddy currents within the conductive shield. These eddy currents generate magnetic fields opposite and nearly equal to the magnetic fields generated by the electromagnetic source. The magnetic fields generated by the eddy currents provide an electromagnetic field which reinforces fields directed towards the body part and diminish electromagnetic fields directed away from the damaged body part.

In another embodiment of the invention, the electromagnetic generator is a bar type dipole, arcuate dipole or compound (such as quadripole). Multiple separate electromagnetic generators are employed in still other embodiments, as well as variations on the spacing of the turns of the conductive coils.

In another embodiment of the present invention, a second piece of high permeability material is placed adjacent to the damaged body part but separated (e.g. diametrically opposed) from the shielded electromagnetic transducer. The presence of the high permeability material creates high electromagnetic flux lines directed towards the high permeability material. The high permeability material behaves as a magnetic conductor much like an electrical conductor alters an electric field. Thus, even more precise direction of the electromagnetic field may be achieved.

By directing the electromagnetic field only to the appropriate damaged body part, large savings in power dissipation are achieved. In addition, the deleterious effects of electromagnetic radiation on healthy tissue are minimized by precise direction of the electromagnetic field.

DESCRIPTION OF THE DRAWINGS

FIG. 14 is a side view diagram of another shielded dipole transducer 100 showing the altered flux lines by the modification of shielded dipole 100 as compared to shielded dipole 10;

FIG. 15 is a side view diagram describing the alteration and the flux lines caused by altering the turn spacing of the coil of shielded dipole 110;

FIG. 16A is an end view diagram showing the positioning of interlocking shielded dipole transducers around invasive bone stabilization equipment (e.g. external fixators) for providing electromagnetic therapy in conjunction with invasive technologies to treat extremely severe broken bones;

FIG. 16B is a top view showing the interlocking shielding of the shielded dipole transducers 122 and 124 of FIG. 16A;

DETAILED DESCRIPTION

Figure 1:
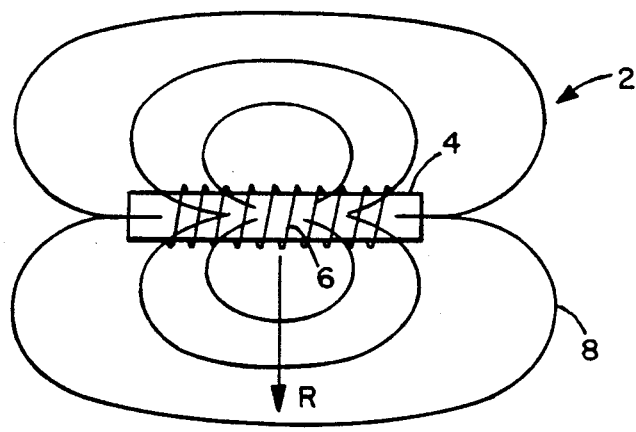
FIG. 1 is a schematic diagram showing the flux lines emanating from a prior art dipole electromagnet.

FIG. 1 is a diagram showing a prior art dipole electromagnet 2. High permeability bar 4 is wrapped by wire 6 a selected number of turns N. When current is passed through windings 6, a magnetic field is generated symbolized by flux lines 8. The intensity of the far magnetic field in a direction perpendicular to dipole 2 is given by the equation:

$$B = \mu_0 n I A / 4\pi R^3$$

where, B is the absolute value of the intensity of the field, $\mu_0$ is the permeability of air, n is the number of turns of winding 6, I is the current passing through winding 6, A is the cross-sectional area of bar 4, R is the distance from the geometric center of bar 4. See Plonus, *Applied Electromagnetics*, p. 328 (1978) McGraw Hill.

A primary goal of the present invention is to efficiently apply electromagnetic energy to a damaged body portion. One major source of waste in the generation of electromagnetic fields is the generation of electromagnetic fields in areas where they are not useful. As can be seen from FIG. 1, an equal amount of the electromagnetic field is generated above and below dipole 2. In fact, the electromagnetic lines of flux forms a toroidal shape centered around the major axis of bar 4.

Figure 2:
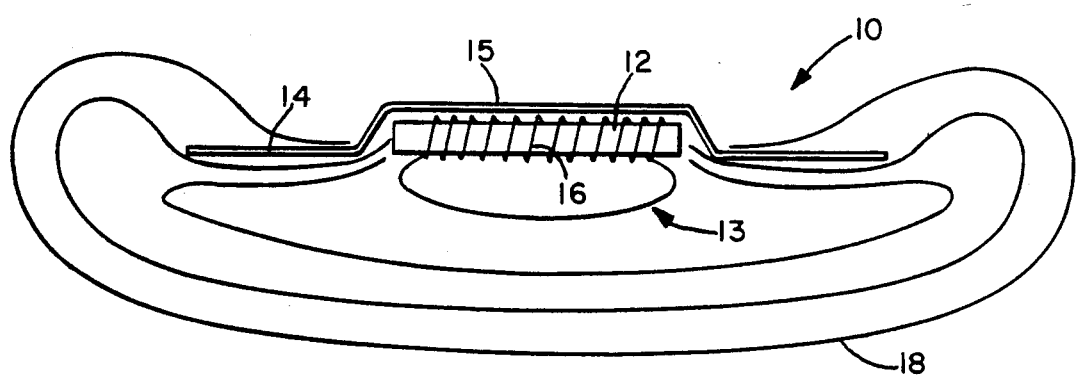
FIG. 2 is a schematic diagram showing the flux lines generated by a dipole transducer in conjunction with a conductive shield.

FIG. 2 is a side view diagram of one embodiment of the present invention showing a shielded dipole arrangement 10. Windings 16 are wrapped around high permeability bar 12 and current is passed through winding 16 to generate a magnetic field represented by flux lines 18. Dipole assembly 13 is positioned inside indentation 15 in conductive plate 14. Conductive plate 14 can be formed of a number of known conductive materials. It is advantageous that the material used to construct conductive plate 14 is as flexible as possible and is as conductive as possible. An ideal conductive plate 14 would be a superconductor material. Unfortunately, the technology of superconductivity has not progressed at this time to a stage where a superconductive material is presently available for this application.

When time varying current passes through winding 16, a time varying magnetic flux is generated. The magnetic flux which attempts to pass through conductive plate 14 induces eddy currents. These eddy currents generate magnetic flux which tends to oppose the magnetic flux which caused the eddy currents in the first place. This principle is known as the Lenz' Law. If conductive plate 14 were a perfect conductor, the magnetic flux generated by the eddy currents would be opposite and equal to the magnetic flux which caused the eddy currents in the first place. Thus, the magnetic flux on the upper side of conductive plate 14 would be completely cancelled and the magnetic flux on the lower side of conductive plate 14 would be reinforced. However, ohmic losses in conductive plate 14 reduce the efficiency so that a partial magnetic field is generated above conductive plate 14. However, the eddy current induced magnetic flux provides a focusing action directing the magnetic field to one side and allows a concentration of the generated magnetic field into a selected body part to aid in the healing process.

Figure 3:
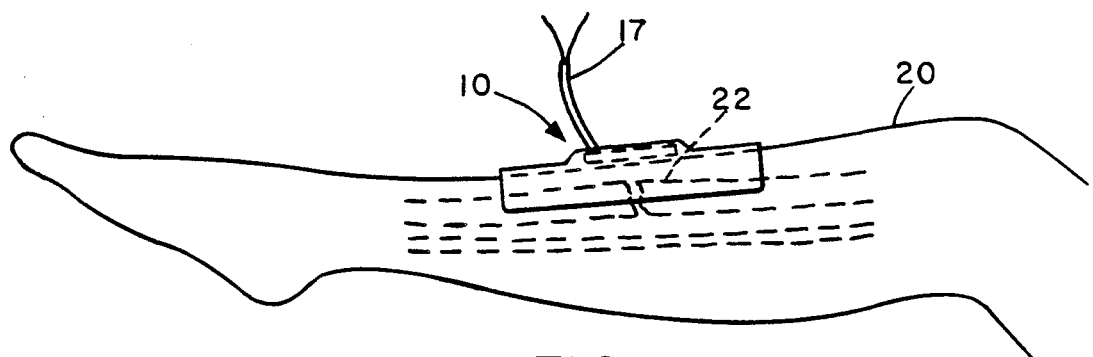
FIG. 3 shows the application of shielded dipole transducer 10 to provide electromagnetic therapy to a broken tibia.

FIG. 3 is a side view diagram showing the placement of shielded dipole transducer 10 on a person's leg to promote the healing of a broken tibia 22. Leads 17 indicate the connection to an electrical source for generating the magnetic field. Experiments have shown that an electrical signal comprised of a train of bursted symmetrical pulses having a frequency of up to 1 megahertz in burst intervals of 5 milliseconds provides optimal power efficiency with effective therapeutic benefit. This signal is provided to leads 17.

Figure 4:
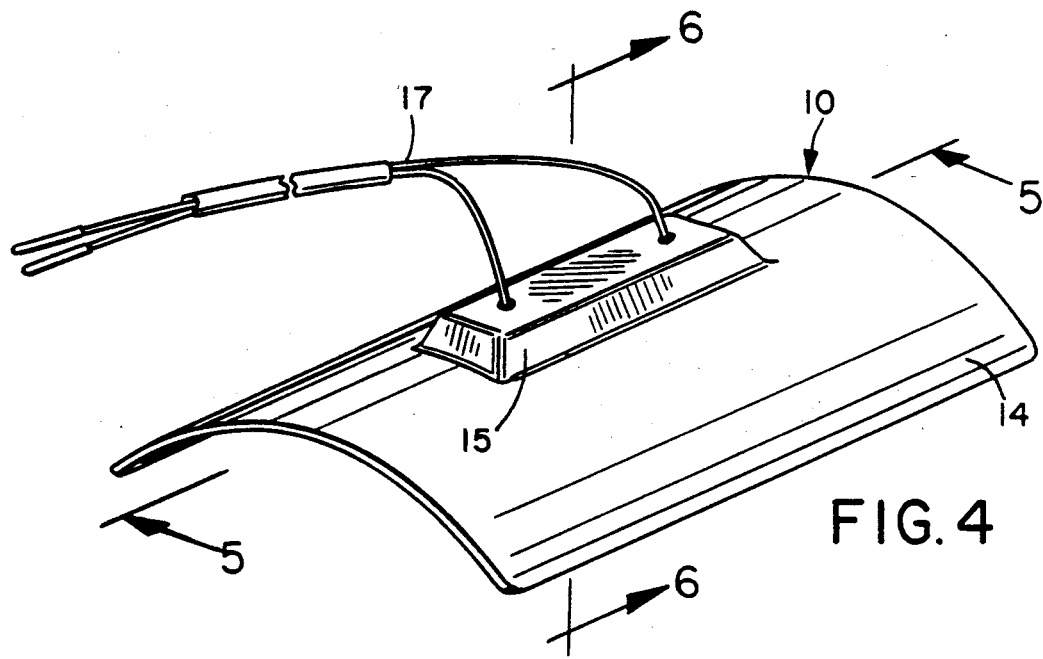
FIG. 4 is a perspective view of the shielded dipole transducer shown in FIG. 2.

FIG. 4 is a perspective view showing the shape of shielded dipole transducer 10.

Figure 5:
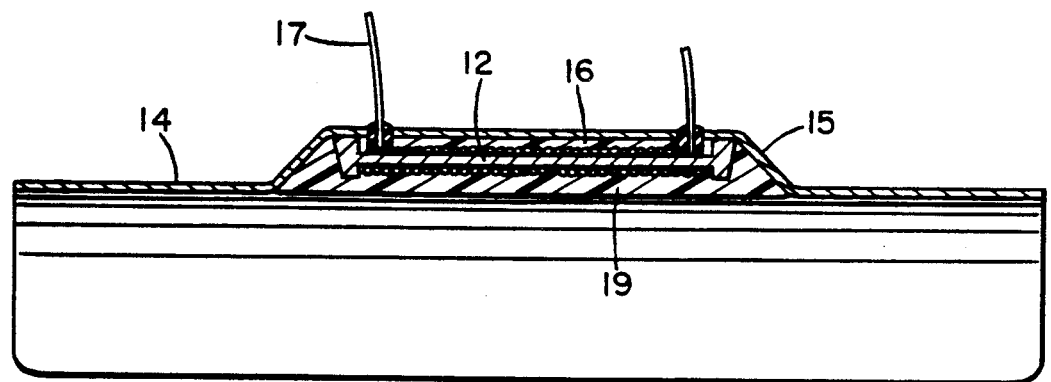
FIG. 5 is cross-sectional view of shielded dipole transducer 10 taken along cross-section line 4 of FIG. 4.
Figure 6:
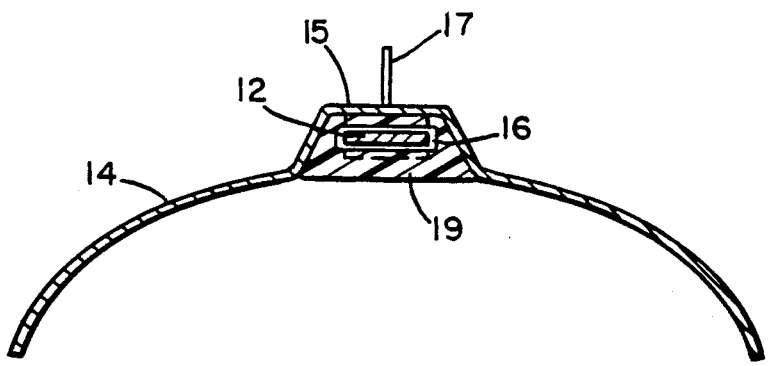
FIG. 6 is another cross-sectional view of shielded dipole 10 taken along section lines 5 of FIG. 4.

FIG. 5 is a cut-away portion along lines 5—5 of FIG. 4 showing the construction of shielded dipole transducer 10. High permeability bar 12 and winding 16 are placed in indentation 15 and indentation 15 is filled with an epoxy material 19 to securely affix bar 12 and winding 16 in indentation 15. Leads 17 are brought out through the surface of field 14 for connection to a power source. An example of a compatible power source for shielded dipole 10 is shown in co-pending application Ser. No. 866,877 of which this application is a continuation-in-part and which is hereby incorporated by reference. FIG. 6 is a cut-away view of transducer 10 an lines 6—6 of FIG. 4.

Figure 7:
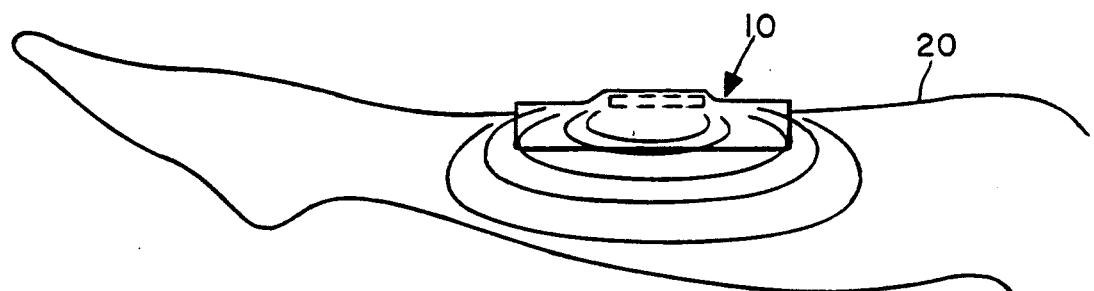
FIG. 7 shows the flux lines generated within the patient's leg by electrical signals applied to the shielded dipole transducer.

FIG. 7 is a side view diagram showing how the electromagnetic field focusing aspects of shielded dipole 10 direct the electromagnetic field to the damaged body portion and maximize the efficiency of the applied energy.

It is important that the size of the shielded dipole transducer be appropriately selected for the depth of penetration required to induce healing in the appropriate body part.

Figure 8:
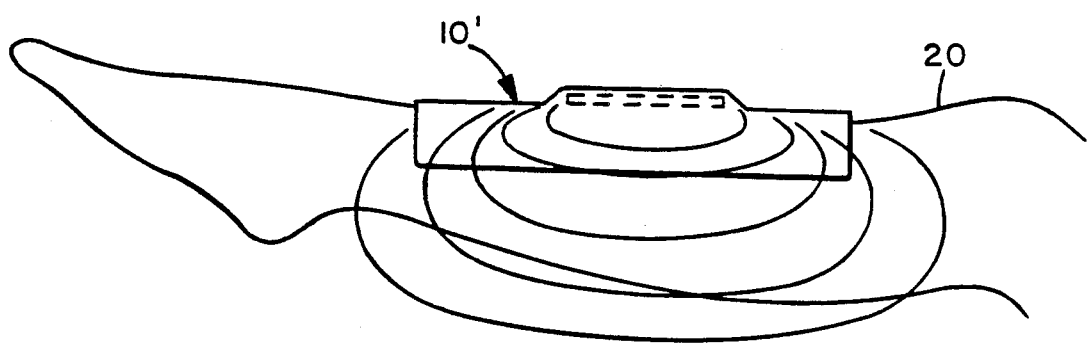
FIG. 8 is a diagram showing the wasted electromagnetic energy generated by an oversized shielded dipole transducer.

As illustrated in FIG. 8, an oversized shielded dipole will generate considerable electromagnetic radiation outside of leg 20 thereby wasting energy. The determination of the intensity of the electromagnetic field of a field generated by a shielded dipole transducer is extremely complex.

Figure 9:
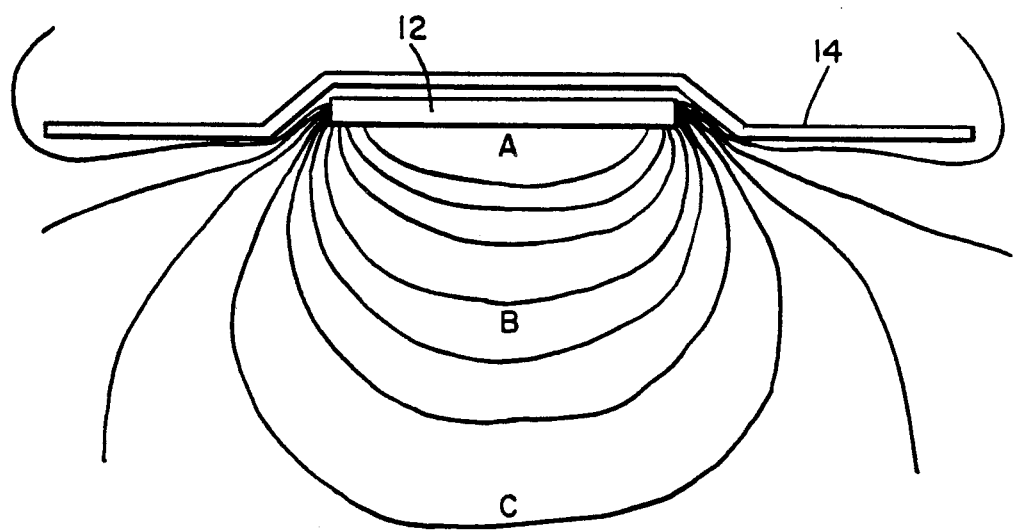
FIG. 9 is a computer generated diagram showing the flux lines of a shielded dipole transducer as calculated by a computer simulation.

FIG. 9 is a drawing taken from a computer generated diagram for synthesizing the electromagnetic field generated by a shielded dipole such as transducer 10. In this model the shield 14 is assumed by the computer to be an ideal conductor. Three points, A, B and C (FIG. 12B) are indicated on the diagram. A indicates the intensity of the electromagnetic field directly beneath shielded dipole 10. B indicates the level where the electromagnetic field corresponds to the minimum effective field for promoting healing. C is an arbitrarily chosen far field point.

Portability is preferably realized by integrating or associating the transducer with the cast around the fracture site, and having the power (battery) source and signal generator located a short distance away. For example, the latter components might be attached to the user's waist belt and connected via leads to the transducer. Alternately, all the components may be attached to or integrated into the cast. The former situation may be favored when a patient needs constant electrostimulation which may necessitate frequent replacement of batteries. On the other hand, for patients with simple or small geometry fractures, the time of application needed for maximum rate of healing may be considerably reduced, and there may be no need to change batteries over the required stimulation period. Here it might be desirable, for convenience to the patient and esthetic purposes, to integrate the entire unit into the cast. Any apparatus installation which minimizes patient involvement or apparatus obtrusiveness, greatly enhances the likelihood of success through improved patient compliance.

It is anticipated that the power source and signal generator circuitry used to generate the therapeutic signal will weigh less than 1 pound and be about the size of a common pocket camera. Typically the battery voltage will be on the order of 6–40 volts and the unit will accommodate a battery having a volume on the order of about 2–60 cubic centimeters. It has been determined that higher voltages are more efficient than lower voltages. However, 40 volts is the generally accepted maximum voltage that can be applied to humans without substantial injury. Present devices operate at 35 volts to allow a five volt margin in case of accidental application of the driving voltage to the patient.

Figure 10A:
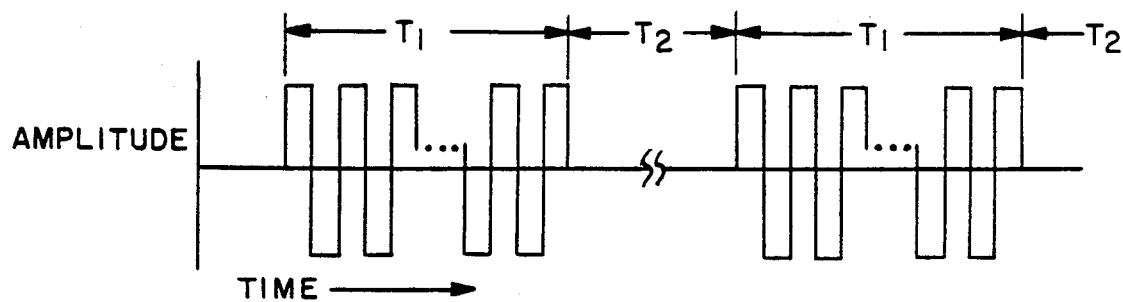
FIGS. 10A and 10B are graphs of representative signals applied to leads 17 of transducer 10.
Figure 10B:
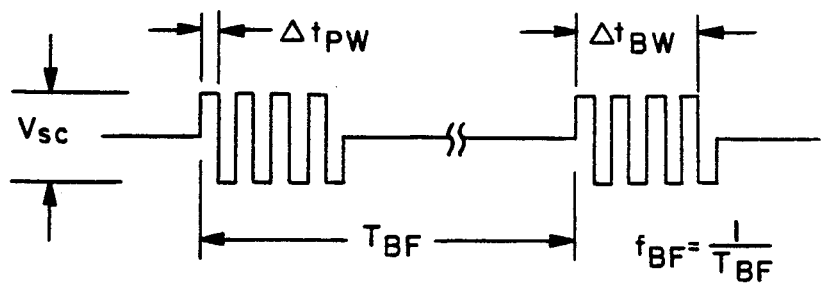

The signal applied to leads 17 is illustrated in FIGS. 10A and 10B. The therapeutic effects of the signal of FIGS. 10A and 10B were established using an animal model system. A reliable animal model for these studies is the rabbit fibular system described by Brighton et al., *J. Orthopaedic Res.*, 3, 331 (1985). In this system, rabbits undergo a mid-shaft transverse osteotomy of one fibula, after which a suitable transducer is placed around the fracture site and connected to a power supply. Both experimental and control animals were treated with the signal shown in FIGS. 10A and 10B where $V_{sc}$ is the search coil voltage; $\Delta t_{PW}$ is pulse width; $\Delta t_{BW}$ is burst width and $f_{BF}$ is burst frequency. The search coil voltage is that voltage which is generated by a time varying magnetic field through a single loop of conductor having an internal area of the loop of one square centimeter.

A $\Delta t_{PW}$ in the range of 0.5–20 μsec, preferably 2–10 μsec, is therapeutically effective, with 5 microseconds being particularly effective. While we do not wish to be bound to any specific theory of operation, we believe that the effectiveness of this invention conforms to theoretical considerations. Activation of the cellular machinery involved in bone repair by electromagnetic radiation requires delivery of a signal to the injured site having defined time constants for burst width and burst frequency. In order to realize this, it is necessary for the signal to be established in healthy tissue and to reach the injured site without being significantly attenuated by the tissue. This in turn suggests that the time constants associated with the magnetic, electric, chemical and electrodiffusion effects caused by the signal exhibit particular time constants. It will be appreciated, referring to Table I below (from Grodzinsky, *Electric Fields, Forces, and Flows in Biological Tissue* (MIT, Lecture Handouts July 1983) and Ohashi et al., "The Electric Current Ratio of the Bone in the Rabbit Thigh for Capacitively Coupled Electric Field," 5th Annual BRAGS (Boston, Mass.; Oct. 13-17, 1985), that the magnetic "diffusion" equation assures that below 100 MHz the magnetic field completely penetrates through to the injured site. For electric "diffusion", penetration of the bone by the displacement current density remains low until 1 MHz (equivalent to $\Delta t_{PW}=0.5$ $\mu$sec). Further, the viscous flow of interstitial fluids in the canaliculi can follow frequencies up to one MHz. In contrast, however, mechanical stress frequency responses attenuate after 500 Hz. Based on this brief analysis, it is apparent that signal current densities with pulses widths as low as 0.5 microseconds would very likely be established in the tissue, and thus potentially produce therapeutically effective results.

Data were derived from experiments in which which time $V_{sc}$, $\Delta t_{PW}$ and duty cycle were varied. Following treatment, both control and experimental animals were sacrificed and the fractured fibula excised. The fibula were mechanically tested for 3 point bending stiffness in a CGS Lawrence testing apparatus as described by Brighton et al., referenced above, and the maximum resistance to bending measured for all the fibulae. The stiffness ratios of the fractured to intact fibulae of the electrically stimulated rabbits were determined and compared to those of the non-stimulated rabbits.

Tables II and III below illustrate the results of the second series of tests with examples of stiffness ratio measurements over a range of and pulse widths given in microseconds at 100 mV (Table II) and search coil voltage $f_B=15$ Hz and $\Delta t_{BW}=5$ msec. Also in both Tables, the average value of the stiffness ratio is denoted by $<x>$ or x, the standard deviation of the test data by SD or $\sigma$ and the number of samples per test by N. The search coil had 67 turns and a diameter of 5.8 mm.

The data in the Tables are readily interpreted from the descriptions of the experiment and the definitions of stiffness ratio given above. Stiffness measures the resistance of an object (e.g., a bone) under a given load; a higher value means a more rigid object. As noted above, the stiffness ratio compares the stiffness of an animal's intact fibula with the stiffness of the fibula of the same animal which has been broken and subsequently healed under the experimental conditions. The higher the stiffness ratio, the more the broken bone has healed and approaches the stiffness of the intact bone; i.e., the better the healing process. It will be evident from the data in Tables II and III that bones healed under the electrotherapy stimulation were more completely healed than the bones of the control animals which had not been subjected to the electrotherapy, as is evidenced by the statistically significant greater stiffness ratios of the treated animals than of the control (non-stimulated) animals.

TABLE I

| PHYSICAL EFFECT | DEFINING EQUATION | $\tau$ TIME CONSTANT | $f_B = \frac{1}{T}$ EQUIVALENT BREAK FREQUENCY | EQUIV. $\Delta t_{PW}$ | PARAMETERS |
| --- | --- | --- | --- | --- | --- |
| MAGNETIC DIFFUSION | $\frac{\delta H}{\delta t} = \frac{1}{\mu\sigma} \nabla^2 H$ | $S^2 \mu \sigma$ | $\frac{2}{(25 \times 10^{-4}) \times 4\pi \times 10^{-7}} \approx 100$ MHZ | 5 nS | $\mu$ = permeability<br>o = conductivity<br>H = field |
| ELECTRIC DIFFUSION | $\nabla \cdot \sigma E = \frac{\delta \rho}{\delta t}$ | $\frac{\epsilon}{\sigma}$ | $\frac{1}{10^{-6}} \approx 1$ MHz | 0.5 $\mu$s | $\epsilon$ = permitivity<br>$\mu$ = permeability |
| VISCOUS DIFFUSION | $\frac{dV}{dt} = \frac{n}{\rho} \nabla^2 V$ | $\frac{\rho R^2}{n}$ | $\frac{10^{-3}}{10^3 (10^{-6})^2} \approx 1$ MHZ | 0.5 $\mu$s | n = viscosity<br>$\rho$ = density<br>R = channel radius<br>(1 $\mu\pi$) |
| MECHANICAL | | $\frac{\delta^2}{mk}$ | $\frac{.5 \times 10^{+6} \times 10^{-15}}{10^3(10^{-6})^2} \approx 500$ Hz | | |

TABLE II

| EXPERIMENT | CONTROL | 2 $\mu$m | 3 $\mu$m | 4 $\mu$s | 5 $\mu$s | 7 $\mu$s | 10 $\mu$m |
| --- | --- | --- | --- | --- | --- | --- | --- |
| 9 May | $<X> = 1.20$<br>SD = 0.78<br>N = 6 | | | | | | $<X> = .366$<br>SD = .194<br>N = 9 |
| 11 June July | $<X> = .236$<br>SD = .147<br>N = 7 | | | | $<X> = .312$<br>SD = .175<br>N = 18 | | |
| 16 Oct. - Nov. | $<X> = .244$<br>SD = .114<br>N = 4 | | | | $<X> = .302$<br>SD = .166<br>N = 5 | | |
| 18 Nov. - Dec. | $<X> = .207$<br>SD = .009<br>N = 2 | | $<X> = .225$<br>SD = .097<br>N = 6 | | $<X> = .216$<br>SD = .156<br>N = 6 | | |
| 19 Jan. | $<X> = .156$<br>SD = .029<br>N = 5 | | $<X> = .265$<br>SD = .204<br>N = 9 | $<X> = .156$<br>SD = .029<br>N = 5 | | | |
| 22 Feb. | $<X> = .156$<br>SD = .030<br>N = 6 | | | | | $<X> = .301$<br>SD = .043<br>N = 7 | |

TABLE III

| EXPERIMENT | CONTROL | 10 mV | 25 mV | 50 mV | 75 mV | 100 mV | 125 mV | 200 mV |
|---|---|---|---|---|---|---|---|---|
| 9 May | $\bar{x}$ = .120<br>$\sigma$ = .078<br>N = 6 | | | | | | | $\bar{x}$ = .266<br>$\sigma$ = .194<br>N = 16 |
| 10 June | $\bar{x}$ = .128<br>$\sigma$ = .044<br>N = 6 | | | | | | | $\bar{x}$ = .142<br>$\sigma$ = .086<br>N = 9 |
| 11 June-July | $\bar{x}$ = .236<br>$\sigma$ = .147<br>N = 7 | | | | | $\bar{x}$ = .312<br>$\sigma$ = .175<br>N = 18 | | |
| 12.5 July-August | $\bar{x}$ = .201<br>$\sigma$ = .097<br>N = 3 | | | $\bar{x}$ = .464<br>$\sigma$ = .074<br>N = 7 | | | | |
| 13.5 August | $\bar{x}$ = .224<br>$\sigma$ =<br>N = 1 | | | $\bar{x}$ = .214<br>$\sigma$ = .079<br>N = 5 | | | | |
| 14 September | $\bar{x}$ = .226<br>$\sigma$ = .107<br>N = 5 | $\bar{x}$ = .189<br>$\sigma$ = .116<br>N = 11 | $\bar{x}$ = .113<br>$\sigma$ = .072<br>N = 3 | | | | | |
| 15 September-October | $\bar{x}$ = .167<br>$\sigma$ = .076<br>N = 4 | | $\bar{x}$ = .177<br>$\sigma$ = .066<br>N = 8 | $\bar{x}$ = .275<br>$\sigma$ = .098<br>N = 6 | $\bar{x}$ = .327<br>$\sigma$ = .148<br>N = 6 | | | |
| 15.5 October | $\bar{x}$ = .288<br>$\sigma$ = .104<br>N = 2 | | | | | $\bar{x}$ = .272<br>$\sigma$ = .201<br>N = 8 | | |
| 16 October-November | $\bar{x}$ = .244<br>$\sigma$ = .114<br>N = 4 | | | | | $\bar{x}$ = .295<br>$\sigma$ = .139<br>N = 7 | $\bar{x}$ = .302<br>$\sigma$ = .166<br>N = 5 | $\bar{x}$ = .359<br>$\sigma$ = .237<br>N = 8 |

Figure 11:
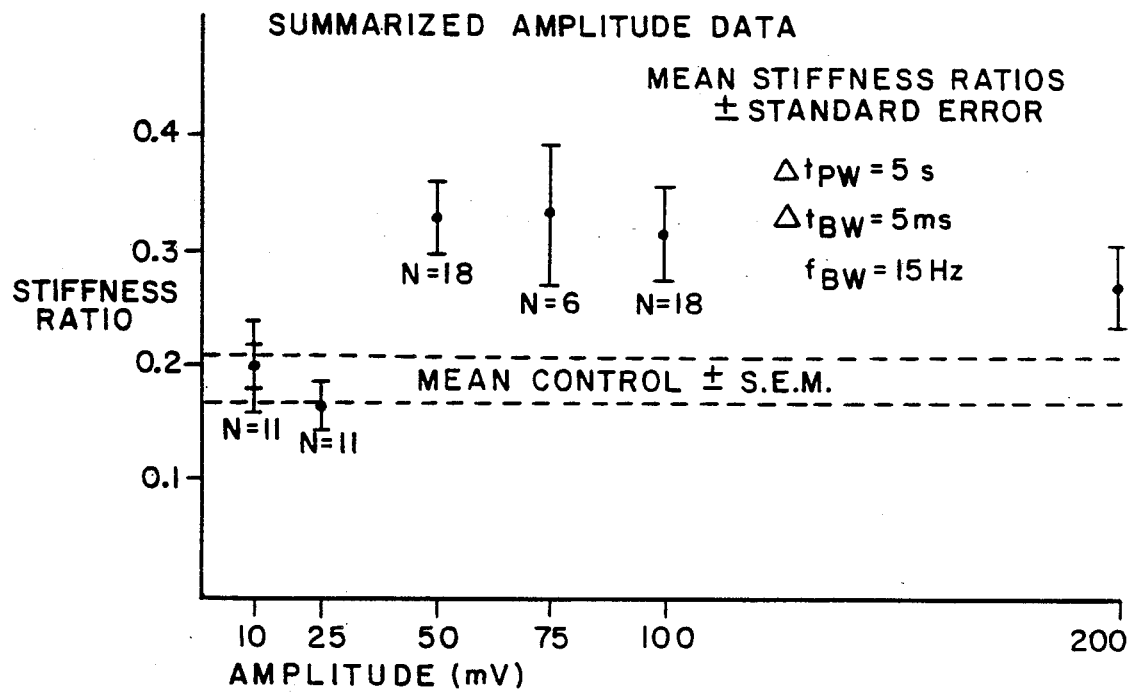
FIG. 11 is a chart showing the stiffness ratios of healed rabbit bones versus the applied search coil voltage.

It will be seen that the procedure is particularly effective when $V_{sc}$ is 74 mV, $\Delta t_{PW}$ is 5 usec, $f_B$ is 15 Hz, $\Delta t_{BW}$ is 5 msec and $t_{PW}$ is varied from 2–10 μsec. Moreover, Table II and FIG. 11 reveal that the effectiveness of these parameters is a function of the amplitude of the signal. A search-coil voltage amplitude of greater than 25 and less than 200 mV is effective with 50–100 being particularly effective.

It will, of course, be appreciated that what has been described is a method for treating certain types of bone fractures. Thus, while the experimental data that support the invention were obtained using rabbits, it is anticipated that with little or no experimentation, the parameters used to effect bone healing are applicable as well to larger animals and to humans. Further, while the data were based on experiments with fresh fractures, it will be appreciated that a signal having the described parameters is able to stimulate healing of various types of bone fractures and damaged tissues, especially bone fractures that do not readily heal in the absence of treatment, such as delayed unions, non-unions and failed fusions.

Figure 12A:
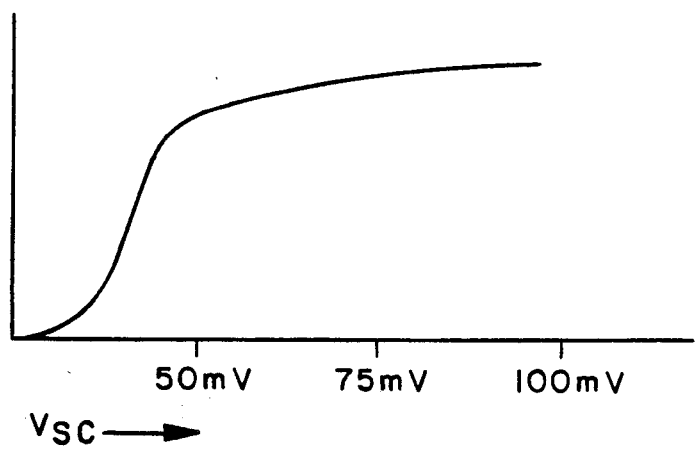
FIG. 12A is a graph showing the relationship between the intensity of the electromagnetic field and the stiffness of the bone treated using electromagnetic therapy.

FIG. 12A is a graph depicting the relative stiffness of osteotomized rabbit bones corresponding to the search coil current used to promote healing in the broken rabbit bones. The vertical scale is a relative scale determined from experimental data shown in Table II. As can be noted in FIG. 12A, a search coil voltage of approximately 50 millivolts is the minimum necessary for significant healing enhancement and a broad range of search coil voltages provides effective therapy. Thus, uniformity of the applied field is not necessary for effective therapy and in fact, because the optimal voltage for each type of cell may vary, a range of applied signals increases the probability that the optimal voltage will stimulate these various cell types and thus enhance the healing process over the prior art teaching of uniform applied fields.

Figure 12B:
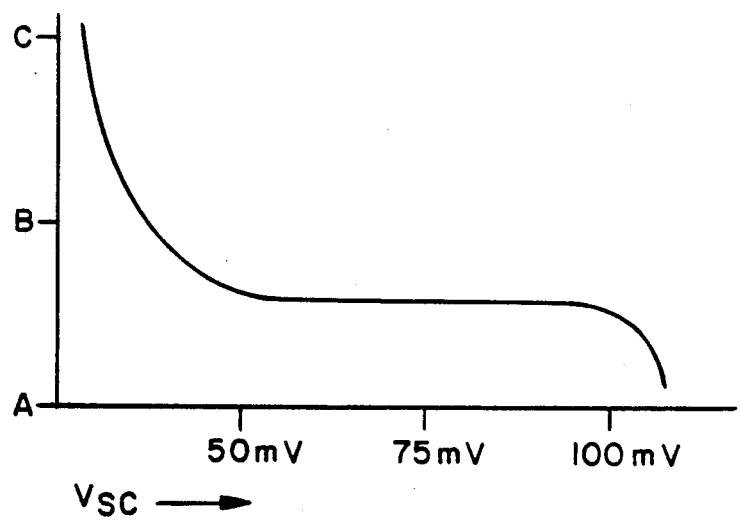
FIG. 12B is a graph showing the intensity of the electromagnetic field generated by a shielded dipole transducer as determined from the computer simulation shown in FIG. 9.

FIG. 12B is a graph depicting the magnetic field generated by the simulation of FIG. 9 in terms of search coil voltage. As can be seen from the graph of FIG. 12B, point B is the farthest point from the shielded dipole which will provide adequate healing electromagnetic fields and that closer points to the shield have a signal which will provide effective therapy. For optimal efficiency, the size of shielded dipole 10 (FIG. 7) should be chosen so that point B is just beyond the damaged body portion in which healing is to be promoted. Table IV is a chart showing the size of bar 12 (FIG. 2) and the corresponding depth of penetration and optimal shield length and shield width.

TABLE IV

| TYPE | BAR LENGTH | DOP (cm) | SHIELD LENGTH | SHIELD WIDTH |
|---|---|---|---|---|
| I | 4 | 2 | 8 | 6 |
| II | 8 | 4 | 16 | 12 |
| III | 12 | 6 | 24 | 18 |

As stated earlier, for maximum utility, the shield 14 should be flexible to allow the molding of the shield to conform to the damaged limb or other damaged body part. However, a conflicting goal is the requirement of maximum conductivity. An extremely thick plate is highly conductive but very inflexible. On the other hand, a thin plate is highly flexible but not very conductive. To determine an adequate compromise, the conductivity of the shield material at operating frequency must be determined. In direct current situations, the conductivity of the shield material is determined by the cross-sectional area of the conductor perpendicular to the direction of current flow. However, for efficient electromagnetic wave generation, the higher the frequency generated, the greater the transfer efficiency into the electromagnetic field. Given a bursted rectangular waveform applied to leads 17 having a pulse width of approximately 5 microseconds, the effective frequency F is $(\frac{1}{2} \times 5\mu S) = 100$ kilohertz. To obtain the Lenz effect for the ninth harmonic, and thus for approximately 90% of the signal, a thickness for the shield must be chosen so that the skin depth at this frequency is about one third of the thickness of the shield. One third of the thickness is for one surface of the shield, another is for the other surface and the third is for additional margin. The skin depth is determined by the equation:

$$D = (FMS)^{-\frac{1}{2}}$$

where,
D is the skin depth,
F is the frequency of the signal,
M is the relative permeability, and
S is the shield material conductivity.
solving these equations for copper and 900 kilohertz yields:
D(Cu)=2.7 mils and thus a shield thickness of 8.1 mils.

The conductive material is preferably a highly conductive material such as copper or aluminum. Aluminum is also advantageous because it is X-ray transmissive. Thus adequate X-rays may be taken through the aluminum shield. Various configurations of shield material have proven efficacious. For example, a wire mesh and a metal foil affixed to a cloth backing has been used. A particularly advantageous embodiment is foil mounted on a cloth backing where a regular pattern of holes, such as diamond shaped holes, are formed in the foil. The holes allow lateral compression of the foil which allows excellent three dimensional conformability to the surface of the injured body portion.

Figure 13A:
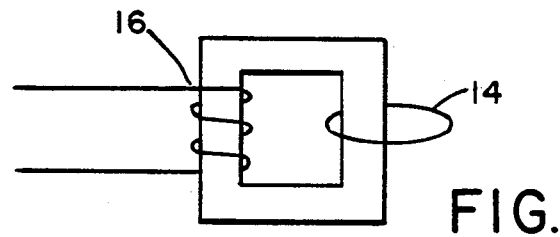
FIG. 13A is a schematic diagram showing an approximate equivalent circuit for shielded dipole 10.
Figure 13B:
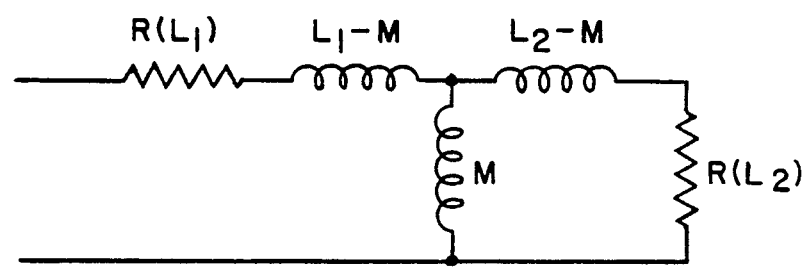
FIG. 13B is a schematic diagram reducing the circuit shown in FIG. 13A to basic circuit elements.

The electrical characteristics of transducer 10 can be expressed as a loosely coupled transformer which is schematically represented by FIG. 13A. Using the T network model for representation of transformers, an equivalent circuit can be shown as in FIG. 13B. $R(L_1)$ is the resistance of coil 16. $L_1$ is the inductance of coil 16. M is the transinductance or coupling of the "transformer." $L_2$ is the inductance of shield 14 and $R(L_2)$ is the resistance of shield 14. Treating the dipole itself as a separate inductor, and assuming that the solenoid has a length to diameter ratio of 1, the inductance in microHenries is given by:

$$L = 6.8SA2$$

where L is the inductance;
S is the diameter of the solenoid; and
n is the number of turns.
Different solenoid configurations require different analysis. Inductive analysis is well known in the art.

The ohmic losses of energy are represented by the ohmic losses passing through $R(L_1)$ and $R(L_2)$. The resistance of the solenoid $(RL_1)$ is determined by taking the unit length resistance of the coil times the total length of the coiled wire. Because shield 14 is loosely coupled, M is nearly equal to 0 and $R(L_2)$ has a nearly direct effect consumption of energy. Therefore, it is very important that the conductivity of shield 14 be maximized. Accurate mathematical models for $R(L_2)$ can only be determined empirically unless very sophisticated computer modeling techniques are used.

FIG. 14 is a technique for enhancing the field distribution of a single dipole shielded dipole transducer. Shielded dipole transducer 100 includes angled end pieces on high permeability bar 104. By angling the end portion away from the shield and towards the surface of the body part under therapy, the magnetic field generated through high permeability bar 104 is directed slightly towards the surface of the body part under therapy. This increases efficiency by directly applying the magnetic field to the body part under therapy and minimizing the field which must be redirected by conductive shield 106.

FIG. 15 is another embodiment of the present invention which tailors the magnetic field by separating the coil around high permeability bar 116 into coils 112 and 114. This creates a flux gap which allows the bulging of the flux field in the center of the dipole. This is another method of tailoring the field beneath shielded dipole 110.

In certain therapy regimens for severe non-union problems, electromagnetic therapy may be used in conjunction with invasive techniques for positioning bones in the proper healing position. A shielded transducer particularly adapted for use with such a therapy regimen is shown in FIG. 16A. Shielded dipole transducers 122 and 124 are positioned on either side of pins 126. Proper positioning of the pins 126 precludes optimal positioning of a single shielded transducer and thus two transducers are used to allow proper application of the electromagnetic field. Pins 126 are usually composed of steel or other conductive materials which alter the electromagnetic fields in the region by the Lenz effect; however, this effect is minimal. Depending on the desired orientation and resultant efficiency, the coils of shielded dipole transducers 122 and 124 will be connected either in series or parallel.

FIG. 16B is a top view of the interleaved relationship of shielded dipole transducers 122, 124 and pins 126. As shown in FIG. 16A, the dipole transducers of shielded dipole transducers 122 and 124 provide complimentary magnetic fields as indicated by the N (for north) and as S (for south) indicators on the dipoles. Alternatively, these dipoles may be wired to generate opposing magnetic fields which may cause desired magnetic field characteristics in certain instances.

Figure 17A:
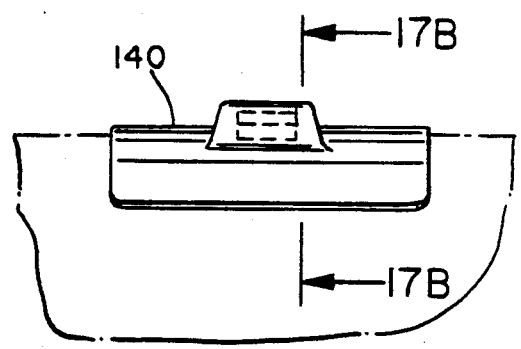
FIG. 17A is an end view diagram showing the positioning of an arcuate shielded dipole transducer on a leg.
Figure 17B:
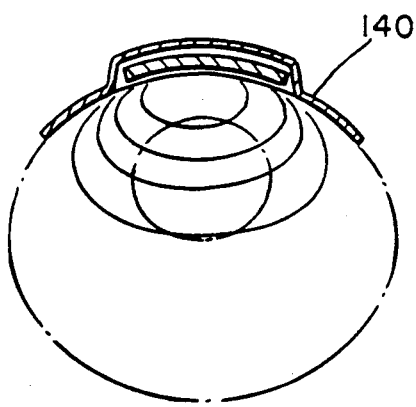
FIG. 17B is a side view diagram showing arcuate transducer 140 positioned on a leg.

FIGS. 17A and 17B show another embodiment of the present invention. Arcuate shielded dipole 140 includes an arcuate dipole to conform to the body part to allow for transverse application of the shielded dipole transducer 140. In certain fractures, such as hairline fractures, the fracture occurs along the major axis of the bone. Although the precise mechanism for enhanced bone growth is not known, some researchers have suggested that applying a field transverse to the fracture generates the physical mechanism which promotes bone growth.

Figure 18A:
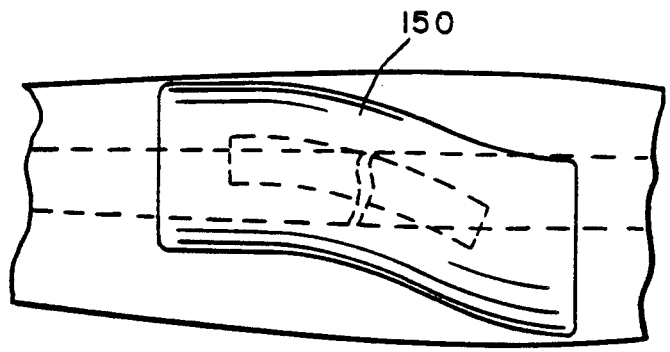
FIG. 18A is a top view diagram showing the positioning of a partially arcuate shielded dipole transducer.
Figure 18B:
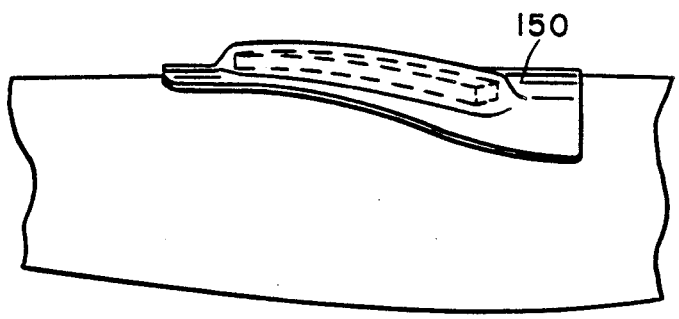
FIG. 18B is a side view diagram of transducer 150 of FIG. 18A.

FIGS. 18A and 18B show another embodiment of the present invention where the dipole itself is twisted and curved around the body part to provide a perpendicular field to an angled fracture.

Figure 19:
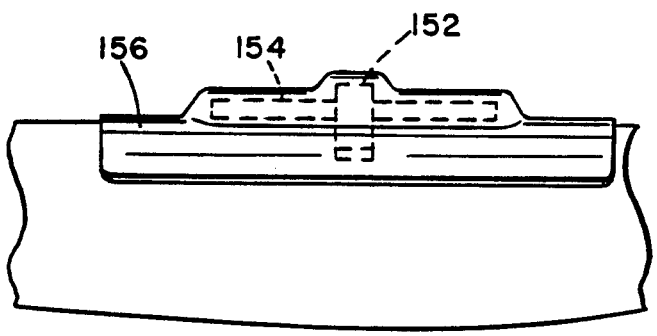
FIG. 19 is a side view diagram showing a quadripole shielded transducer.

FIG. 19 is a quadripole shielded transducer including an arcuate dipole 152 and a linear dipole 154, both shielded by conductive shield 156. In certain instances, the complex magnetic fields generated by the two dipoles may prove beneficial.

Figure 20:
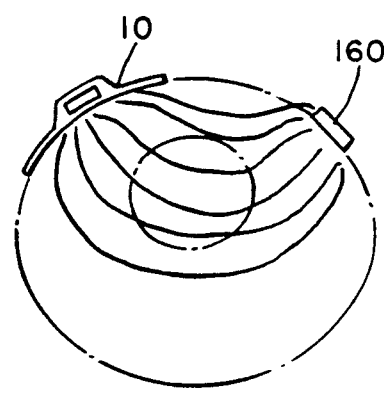
FIG. 20 is an end view diagram showing the lines of flux for positioning a portion of high permeability material in the vicinity of the operation of shielded dipole 10.

FIG. 20 shows another embodiment of the present invention wherein shielded dipole 10 is positioned near high permeability piece 160. High permeability piece 160 may also be positioned diametrically opposed to shielded dipole 10. The positioning of high permeability piece 160 alters the magnetic flux like the presence of a conductor alters the electrical flux in an electrical field. The field altering characteristics of the positioning of high permeability piece 160 can aid in directing the magnetic field towards the desired body portion or modify the field distribution.

Although specific embodiments of the present invention are herein disclosed, they are not to be construed as limiting the scope of the invention. For example, although devices shown for generating magnetic fields from electrical current are coils surrounding high permeability material, any electrical to electromagnetic transducer is useful in conjunction with the present invention and is another embodiment of the present invention. The scope of the invention is only limited by the claims appended hereto.

I claim:

1. A transducer for converting an electrical signal into an electromagnetic field for application of said electromagnetic field to a damaged body part to promote healing of said body part, said transducer comprising a conductive coil, said coil having first and second terminals at opposite ends of said coil, said first and second terminals connected to receive said electrical signal, said coil providing an electromagnetic field in response to said electrical signal and said coil providing said electromagnetic field to said damaged body part when placed proximal to said damaged body part; and a conductive plate adapted to be positioned adjacent to said conductive coil and opposite from said damaged body part, said plate having a major surface adapted to be positioned parallel to said damaged body part and said plate extending laterally beyond said conductive coil in the direction of said major surface.

2. A transducer as in claim 1 wherein said plate includes an indentation adapted for said coil, said major surface of said plate being closer to said damaged body part in the area extending beyond said coil than the area of said major surface of said plate not extending beyond said conductive coil.

3. A transducer as in claim 2 where in said area extending beyond said coil of said major surface of said conductive plate is substantially flush with the surface of said coil nearest said damaged body part 4. A transducer as in claim 1 where said conductive plate is flexible.

5. A transducer as in claim 4 where said flexible conductive plate comprises a mesh of conductive wire.

6. A transducer as in claim 1 wherein said conductive plate comprises a layer of conductive and malleable material affixed to a flexible backing, said layer having a regular pattern of holes formed therein.

7. A transducer for converting an electrical signal into an electromagnetic field for application of said electromagnetic field to a damaged body part to promote healing of said body part, said transducer comprising:

a core piece comprising high permeability material;

a conductive coil wrapped around said core piece, said coil having first and second terminals at opposite ends of said coil, said first and second terminals connected to receive said electrical signal, said coil and said core piece providing an electromagnetic field in response to said electrical signal and said coil and core piece providing said electromagnetic field to said damaged body part when placed proximal to said damaged body part; and a conductive plate adapted to be positioned adjacent to said core piece and conductive coil and opposite from said damaged body part, said plate having a major surface adapted to be positioned parallel to said damaged body part and said plate extending laterally beyond said core piece and conductive coil in the direction of said major surface.

8. A transducer as in claim 7 wherein said plate includes an indentation adapted for said core piece and coil, said major surface of said plate being closer to said damaged body part in the area extending beyond said core piece and conductive coil than the area of said major surface of said plate not extending beyond said core piece and conductive coil.

9. A transducer as in claim 8 where in said area extending beyond said core piece and coil of said major surface of said conductive plate is substantially flush with the surface of said core piece and coil nearest said damaged body part.

10. A transducer as in claim 7 wherein the surfaces of said core piece intersecting a line which runs perpendicularly to the planes formed by the loops of said conductive coil form an obtuse angle with the surface of said core piece adjacent to said damaged body part.

11. A transducer as in claim 7 where said conductive plate is flexible.

12. A transducer as in claim 11 where said flexible conductive plate comprises a mesh of conductive wire 13. A transducer as in claim 7 wherein said conductive plate comprises a layer of conductive and malleable material affixed to a flexible backing, said layer having a regular pattern of holes formed therein.

14. A transducer for converting an electrical signal into an electromagnetic field for application of said electromagnetic field to a damaged body part to promote healing of said body part, said transducer comprising:

a plurality of core pieces comprising high permeability material;

a conductive coil wrapped around said core pieces, said coil having first and second terminals at opposite ends of said coil, said first and second terminals connected to receive said electrical signal, said coil and said core pieces providing an electromagnetic field in response to said electrical signal and said coil and core piece providing said electromagnetic field to said damaged body part when placed proximal to said damaged body part; and a plurality of conductive plates one for each of said core pieces adapted to be positioned adjacent to said core pieces and conductive coil and opposite from said damaged body part, said plates having a major surface adapted to be positioned parallel to said damaged body part and said plates extending beyond said core piece and conductive coil in the direction of said major surface.

15. A transducer as in claim 14 wherein said plates include an indentation adapted for said core piece and coil, said major surface of said plates being closer to said damaged body part in the area extending beyond said core pieces and conductive coil than the area of said major surface of said plate not extending beyond said core pieces and conductive coil.

16. A transducer as in claim 15 where in said area extending beyond said core piece and coil of said major surface of said conductive plate is substantially flush with the surface of said core pieces and coil nearest said damaged body part.

17. A transducer as in claim 14 wherein the surfaces of said core pieces intersecting a line which runs perpendicularly to the planes formed by the loops of said conductive coil form an obtuse angle with the surface of said core piece adjacent to said damaged body part.

18. A transducer as in claim 14 where said conductive plate is flexible.

19. A transducer as in claim 18 where said flexible conductive plate comprises a mesh of conductive wire.

20. A transducer as in claim 14 wherein said conductive plates interlock to provide a single mechanically integrated structure.

21. A transducer as in claim 14 wherein said coil is wound in one direction on one core piece and in the opposite direction on an adjacent core piece to provide opposing magnetic fields.

22. A transducer as in claim 14 wherein said coil is wrapped in the same direction on said core pieces 23. A transducer as in claim 14 wherein said conductive plate comprises a layer of conductive and malleable material affixed to a flexible backing, said layer having a regular pattern of holes formed therein.

24. A transducer for converting an electrical signal into an electromagnetic field for application of said electromagnetic field to a damaged body part to promote healing of said body part, said transducer comprising:
   first and second core pieces comprising high permeability material;
   a conductive coil wrapped around said first and second core pieces, said coil having first and second terminals at opposite ends of said coil, said first and second terminals connected to receive said electrical signal, said coil and said first and second core pieces providing perpendicular electromagnetic fields in response to said electrical signal and said coil and core piece providing said electromagnetic field to said damaged body part when placed proximal to said damaged body part; and
   a conductive plate adapted to be positioned adjacent to said first and second core pieces and conductive coil, and opposite from said damaged body part, said plate having a major surface adapted to be positioned parallel to said damaged body part and said plate extending laterally beyond said first and second core pieces and conductive coil in the direction of said major surface.

25. A transducer as in claim 24 wherein said plate includes an indentation adapted for said first and second core pieces and coil, said major surface of said plate being closer to said damaged body part in the area extending beyond said first and second core pieces and conductive coil than the area of said major surface of said plate not extending beyond said core piece and conductive coil.

26. A transducer as in claim 25 where in said area extending beyond said core piece and coil of said major surface of said conductive plate is substantially flush with the surface of said first and second core pieces and said coil nearest said damaged body part.

27. A transducer as in claim 24 wherein the surfaces of said first and second core pieces intersecting a line which runs perpendicularly to the planes formed by the loops of said conductive coil form an obtuse angle with the surface of said first and second core pieces adjacent to said damaged body part.

28. A transducer as in claim 24 where said conductive plate is flexible.

29. A transducer as in claim 28 where said flexible conductive plate comprises a mesh of conductive wire.

30. A transducer as in claim 24 wherein said conductive plate comprises a layer of conductive and malleable material affixed to a flexible backing, said layer having a regular pattern of holes formed therein.

31. A transducer for converting an electrical signal into an electromagnetic field for application of said electromagnetic field to a damaged body part to promote healing of said body part, said transducer comprising:
   a core piece comprising high permeability material said core piece being curved to conform to said damaged body part;
   a conductive coil wrapped around said core piece, said coil having first and second terminals at opposite ends of said coil, said first and second terminals connected to receive said electrical signal, said coil and said core piece providing an electromagnetic field in response to said electrical signal and said coil and core piece providing said electromagnetic field to said damaged body part when placed proximal to said damaged body part; and
   a conductive plate adapted to be positioned adjacent to said core piece and conductive coil and opposite from said damaged body part, said plate having a major surface adapted to be positioned parallel to said damaged body part and said plate extending beyond said core piece and conductive coil in the direction of said major surface 32. A transducer as in claim 31 wherein said plate includes an indentation adapted for said core piece and coil, said major surface of said plate being closer to said damaged body part in the area extending beyond said core piece and conductive coil than the area of said major surface of said plate not extending beyond said core piece and conductive coil.

33. A transducer as in claim 32 where in said area extending beyond said core piece and coil of said major surface of said conductive plate is substantially flush with the surface of said core piece and coil nearest said damaged body part.

34. A transducer as in claim 31 wherein the surfaces of said core piece intersecting a line which runs perpendicularly to the planes formed by the loops of said conductive coil form an obtuse angle with the surface of said core piece adjacent to said damaged body part.

35. A transducer as in claim 31 where said conductive plate is flexible.

36. A transducer as in claim 35 where said flexible conductive plate comprises a mesh of conductive wire.

37. A transducer as in claim 31 wherein said conductive plate comprises a layer of conductive and malleable material affixed to a flexible backing, said layer having a regular pattern of holes formed therein.

38. A transducer for converting an electrical signal into an electromagnetic field for application of said electromagnetic field to a damaged body part to promote healing of said body part, said transducer comprising
   a core piece comprising high permeability material;
   a conductive coil wrapped around said core piece, said coil having first and second terminals at opposite ends of said coil, said first and second terminals connected to receive said electrical signal, said coil and said core piece providing an electromagnetic field in response to said electrical signal and said coil and core piece providing said electromagnetic field to said damaged body part when placed proximal to said damaged body part;
   a shunt piece of high permeability material placed adjacent to said damage body part; and a conductive plate adapted to be positioned adjacent to said core piece and conductive coil and opposite from said damaged body part, said plate having a major surface adapted to be positioned parallel to said damaged body part and said plate extending beyond said core piece and conductive coil in the direction of said major surface.

39. A transducer as in claim 38 wherein said plate includes an indentation adapted for said core piece and coil, said major surface of said plate being closer to said damaged body part in the area extending beyond said core piece and conductive coil than the area of said major surface of said plate not extending beyond said core piece and conductive coil.

40. A transducer as in claim 39 where in said area extending beyond said core piece and coil of said major surface of said conductive plate is substantially flush with the surface of said core piece and coil nearest said damaged body part.

41. A transducer as in claim 38 wherein the surfaces of said core piece intersecting a line which runs perpendicularly to the planes formed by the loops of said conductive coil form an obtuse angle with the surface of said core piece adjacent to said damaged body part.

42. A transducer as in claim 38 where said conductive plate is flexible.

43. A transducer as in claim 42 where said flexible conductive plate comprises a mesh of conductive wire.

44. A transducer as in claim 38 wherein said conductive plate comprises a layer of conductive and malleable material affixed to a flexible backing, said layer having a regular pattern of holes formed therein.

45. A transducer for converting an electrical signal into an electromagnetic field for application of said electromagnetic field to a damaged body part to promote healing of said body part, said transducer comprising:

a core piece comprising high permeability material;

a plurality of electrically connected conductive coils wrapped around said core piece, said plurality of coils having first and second terminals at opposite ends of said plurality of coils, said first and second terminals connected to receive said electrical signal, said plurality of coils and said core piece providing an electromagnetic field in response to said electrical signal and said plurality of coils and core piece providing said electromagnetic field to said damaged body part when placed proximal to said damaged body part; and a conductive plate adapted to be positioned adjacent to said core piece and plurality of conductive coils and opposite from said damaged body part, said plate having a major surface adapted to be positioned parallel to said damaged body part and said plate extending beyond said core piece and plurality of conductive coils in the direction of said major surface.

46. A transducer as in claim 45 wherein said plate includes an indentation adapted for said core piece and said plurality of coils, said major surface of said plate being closer to said damaged body part in the area extending beyond said core piece and said plurality of conductive coils than the area of said major surface of said plate not extending beyond said core piece and plurality of conductive coils.

47. A transducer as in claim 46 where in said area extending beyond said core piece and plurality of conductive coils of said major surface of said conductive plate is substantially flush with the surface of said core piece and said plurality of conductive coils nearest said damaged body part.

48. A transducer as in claim 45 wherein the surfaces of said core piece intersecting a line which runs perpendicularly to the planes formed by the loops of said plurality of conductive coils form an obtuse angle with the surface of said core piece adjacent to said damaged body part.

49. A transducer as in claim 45 where said conductive plate is flexible.

50. A transducer as in claim 48 where said flexible conductive plate comprises a mesh of conductive wire.

51. A transducer as in claim 45 wherein said conductive plate comprises a layer of conductive and malleable material affixed to a flexible backing, said layer having a regular pattern of holes formed therein.

* * * * *